(12) United States Patent
Lutz et al.

(10) Patent No.: US 7,289,231 B2
(45) Date of Patent: Oct. 30, 2007

(54) APPARATUS AND METHOD FOR DETERMINING PHYSICAL PROPERTIES OF A MASK BLANK

(75) Inventors: Tarek Lutz, München (DE); Markus Menath, Regensburg (DE)

(73) Assignee: Infineon Technologies AG, Munich (DE)

( * ) Notice: Subject to any disclaimer, the term of this patent is extended or adjusted under 35 U.S.C. 154(b) by 338 days.

(21) Appl. No.: 10/744,067

(22) Filed: Dec. 24, 2003

(65) Prior Publication Data

US 2004/0194039 A1 Sep. 30, 2004

(30) Foreign Application Priority Data

Dec. 27, 2002 (DE) ................. 102 61 323

(51) Int. Cl.
- *G01B 11/14* (2006.01)
- *G01B 11/16* (2006.01)
- *G01N 21/00* (2006.01)
- *G01N 21/86* (2006.01)
- *G01V 8/00* (2006.01)
- *G06K 9/00* (2006.01)

(52) U.S. Cl. ............... 356/625; 356/32; 356/337; 356/432; 356/237.1; 356/239.1; 250/559.4; 382/144

(58) Field of Classification Search .............. None
See application file for complete search history.

(56) References Cited

U.S. PATENT DOCUMENTS

| | | | | |
|---|---|---|---|---|
| 4,610,541 A | * | 9/1986 | Tanimoto et al. | 356/239.8 |
| 4,958,083 A | * | 9/1990 | Sakamoto | 250/559.41 |
| 6,479,196 B2 | * | 11/2002 | Levenson | 430/5 |
| 6,627,362 B2 | * | 9/2003 | Stivers et al. | 430/5 |
| 6,858,859 B2 | * | 2/2005 | Kusunose | 250/559.45 |
| 2005/0057747 A1 | * | 3/2005 | Meeks | 356/237.3 |

FOREIGN PATENT DOCUMENTS

JP 09260468 A * 10/1997

* cited by examiner

Primary Examiner—Gregory J. Toatley, Jr.
Assistant Examiner—Gordon J. Stock, Jr.
(74) Attorney, Agent, or Firm—Morrison & Foerster LLP

(57) ABSTRACT

An apparatus for determining physical properties of a mask blank. The apparatus includes, for example, an illumination device for radiating a predetermined light laterally into the mask blank, a detection device opposite the illumination device for detecting the light which has been scattered and/or runs through the mask blank, and an evaluation device for determining predetermined properties of the mask blank from the light which has been scattered and/or has run through the mask blank and has been detected in the detection device. The present invention likewise provides a method for determining physical properties of a mask blank.

18 Claims, 2 Drawing Sheets

APPARATUS AND METHOD FOR DETERMINING PHYSICAL PROPERTIES OF A MASK BLANK

CLAIM FOR PRIORITY

This application claims the benefit of priority to German Application No. 102 61 323.0, filed in the German language on Dec. 27, 2002, the contents of which are hereby incorporated by reference.

TECHNICAL FIELD OF THE INVENTION

The present invention relates to an apparatus and a method for determining physical properties of a mask blank, and in particular to an apparatus and a method for determining mechanical stresses and/or flexures of a mask blank.

BACKGROUND OF THE INVENTION

Mask blanks are used in machining tools for manufacturing integrated circuits in order to serve as an exposure mask for example in a stepper device. Usually, a mask blank comprises a carrier device, preferably made of glass having a thickness of about 6 mm, to which is applied a molybdenum-silicon nitride layer preferably having a thickness of 100 nm and, over the latter, a chromium layer likewise having a thickness of 100 nm as hard mask. Arranged above that is a photoresist layer having a thickness of 500 nm, for example.

In order to be able to serve as a patterned mask, the mask blank or the layers deposited on the glass must be patterned in various machining steps. This patterning is effected for example in pattern generators. For this purpose, the mask blank is quite generally clamped in a fixing or clamping device. Customary clamping devices clamp a mask blank by means of mechanical spring elements. This often leads to mechanical stresses or flexures of the mask blank and thus to a reduced quality of the patterned mask.

Hitherto, such dislocations and strains have only been detected or identified at the end of the process for producing the mask blank or the mask in the form of registration fluctuations, accuracy or position fluctuations and other faults. Mask blanks which lie outside a tolerance range have to be separated out by sorting.

SUMMARY OF THE INVENTION

The present invention provides an apparatus and a method for determining physical properties of a mask blank, whereby the quality assurance and/or inspection of the mask blanks is simplified and in situ determination is made possible.

The present invention essentially includes generating a tomogram of a mask blank by introducing a predetermined light and detecting the light which has been scattered in the mask blank, thereby localizing scattering sources for example as a result of flexures, mechanical stresses caused by the absorber layer or as a result of clamping the mask blank or on account of inclusions or impurity particles.

In the present invention, the problem mentioned in the introduction is solved, in one embodiment, by providing an apparatus for determining physical properties of a mask blank having an illumination device for radiating a predetermined light laterally into the mask blank; a detection device opposite the illumination device for detecting the light which has been scattered and/or runs through the mask blank; and an evaluation device for determining physical properties of the mask blank from the light which has been scattered and/or has run through the mask blank and has been detected in the detection device.

In this way, a tomogram of the mask blank is generated in the evaluation device, preferably a computer, thereby characterizing predetermined properties or the state of the mask blank.

In accordance with one preferred embodiment, the illumination device has a laser device or laser diodes.

In accordance with a further preferred embodiment, the illumination device, the mask blank and the detection device are accommodated in a mask production tool.

In accordance with a further preferred embodiment, the illumination device and the detection device are arranged such that they are diametrically opposite and rotatable by at least 180° in the plane of the mask blank around the mask blank situated inbetween.

In accordance with a further preferred embodiment, the illumination device and the detection device are arranged pointing inward in a recess, in which the mask blank is arranged.

In accordance with a further preferred embodiment, laser diodes as illumination device and laser detectors as detection device are arranged alternately next to one another, in which case, preferably, the laser diodes are connected in series and the light which runs through the mask blank can be detected simultaneously by the laser detectors.

In accordance with a further preferred embodiment, a data analysis of the light detected by the detection device on the basis of a Fourier transformation for the purpose of creating a characteristic of the mask blank can be provided in the evaluation device.

In accordance with a further preferred embodiment, the mask blank is fixed in a fixing device with an adjustable clamping force.

In accordance with a further preferred embodiment, the fixing of the mask blank in the fixing device is provided by piezoelements, preferably tube piezoelements.

In accordance with a further preferred embodiment, the clamping force of the fixing device of the mask blank is adjustable depending on the evaluated predetermined properties of the mask blank.

In accordance with a further preferred embodiment, the fixing device of the mask blank has at least three separately drivable clamping elements, preferably piezoelements.

In accordance with a further preferred embodiment, scattering sources, such as, for example, inclusions or mechanical stresses and/or flexures in the mask blank are calculated and localized in the evaluation device on the basis of the received data of the detection device.

In accordance with a further preferred embodiment, on the basis of the data of localized scattering source brought about by a mechanical flexure, an adjustable fixing device, which clamps the mask blank, is driven in such a way that the flexure is reduced.

In accordance with a further preferred embodiment, the detection of the light which runs through the mask blank in the detection device is effected by utilizing the Kerr effect.

BRIEF DESCRIPTION OF THE DRAWINGS

Exemplary embodiments of the invention are illustrated in the drawings and explained in more detail in the description below.

In the figures.

In the figures, identical reference symbols designate identical or functionally identical constituent parts.

DETAILED DESCRIPTION OF THE INVENTION

Figure 1:
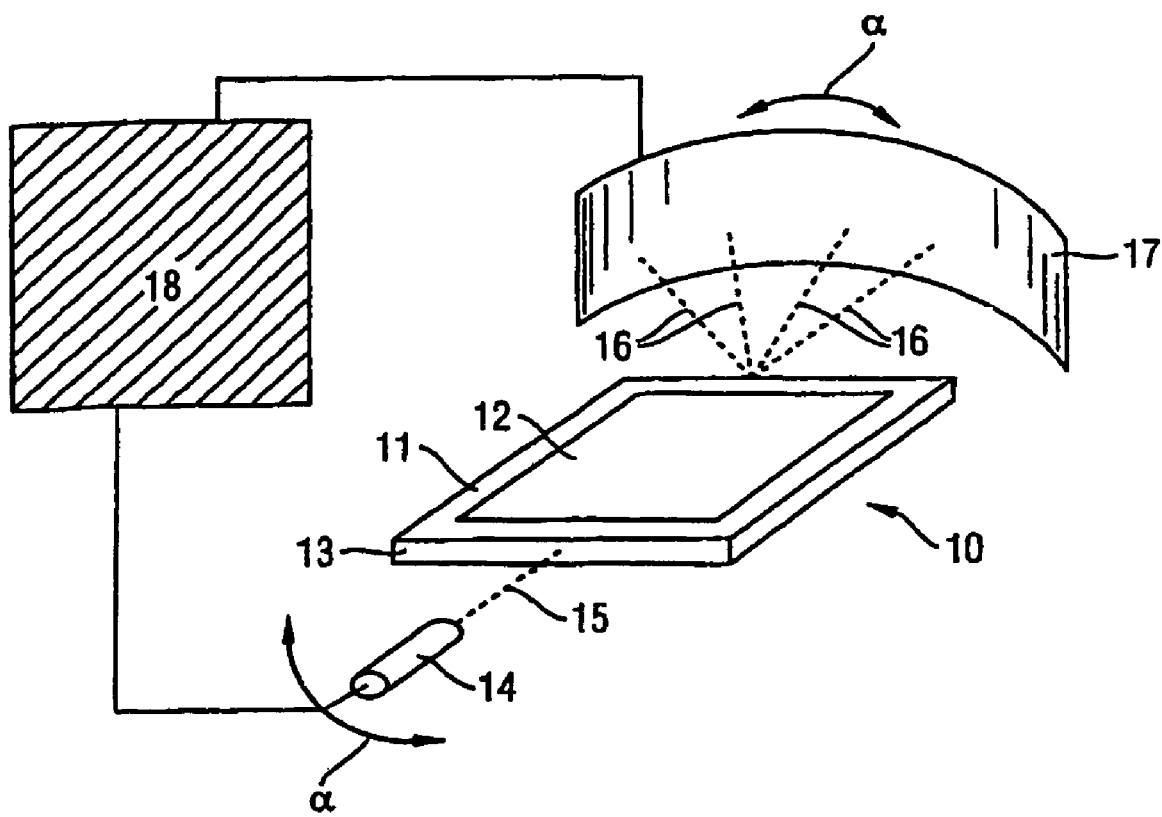
FIG. 1 shows a diagrammatic oblique view of an apparatus for determining physical properties of a mask blank for elucidating a first embodiment of the present invention.

FIG. 1 illustrates a mask blank 10, which essentially comprises a carrier device 11, e.g. a glass body having a thickness of about 6 mm with a rectangular base area, and a layer sequence 12 deposited thereon. The layer sequence 12 on the carrier device 11 has, by way of example, a molybdenum-silicon nitride layer, at the periphery a chromium layer and in the vertical direction a terminating photoresist layer.

An illumination device 14 oriented toward a side area 13 of the mask blank 10, preferably a laser, radiates a predetermined light 15 into the mask blank 10 essentially perpendicularly to the side wall 13 of the mask blank 10. The light 15, running essentially parallel to the layer sequence 12, runs through the mask blank 10 and is if appropriate scattered at dislocations, strains, other deformations such as mechanical stresses or flexures or at defects or impurity particles in the mask blank 10. Light 16 which runs through the mask blank 10 or is scattered therein is received in a detection device 17. The detection device 17 is diametrically opposite the illumination device 14, the mask blank 10 being arranged such that it lies inbetween. The illumination device 14, the detection device 17 and the mask blank 10 lie in one plane.

In order now to be able to create a tomogram or a map of the blank interior the illumination device 14 coupled with the detection device 17 is moved at least by an angle α of at least 180° around the mask blank 10, so that in an evaluation device 18, e.g. a computer, scattering sources present in the blank material and the position of said scattering sources can be computationally deduced from the combination of the emitted and detected light beams 15, 16.

The laser light 16 scattered in the mask blank 10 is stored in a location-dependent manner in the computer 18. The blank map thus generated may then be used as a reference for any further tool (pattern generator, metrology, etc.) or as a basis for corrections. A map generated in this way is likewise suitable for identifying the mask blank quality, in which case this determination of the predetermined properties such as e.g. mask blank flexures and included particles in the mask blank 10 may likewise be carried out during the machining process of a mask blank 10 in a blank machining tool.

An evaluation of the data of the detection device 17 in the evaluation device 18 is preferably effected on the basis of a Fourier transformation. The evaluation device 18 not only processes and analyzes the data of the detection device 17 but preferably likewise controls the illumination device 14 and thus the incident light 15.

Figure 2:
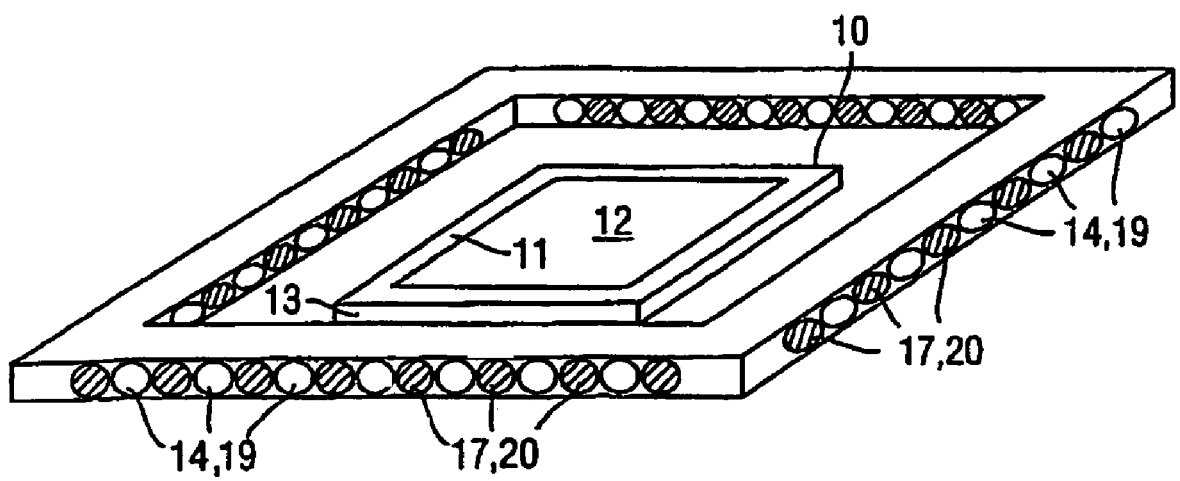
FIG. 2 shows a diagrammatic oblique view of an apparatus for determining physical properties of a mask blank for elucidating a second embodiment of the present invention.

In a second embodiment in accordance with FIG. 2, the mask blank 10 is identical to the mask blank described with reference to FIG. 1. In accordance with the second embodiment, an illumination device 14 comprises a plurality of light sources 19, e.g. laser diodes. A detection device 15 likewise comprises a plurality of detectors 20, preferably laser detectors, which, like the laser diodes 19, are arranged in a manner distributed around the mask blank 10 in one plane with the mask blank 10. The illumination device 14 and the detection device 17 are preferably arranged internally in a recess 21 for receiving the mask blank 10, both the illumination device 14 and the detection device 17 being positioned essentially perpendicularly to the side areas 13 of the mask blank 10.

The laser diodes 19 and the laser detectors 20 are preferably arranged alternately next to one another. The laser diodes 19 are connected in series, and the detectors 20 simultaneously receive the laser scattering waves which have been scattered in the mask blank 10. The data supplied by the detectors 20 are preferably detected or evaluated by utilizing the Kerr effect. In this case, too, as described with reference to FIG. 1, a data analysis of the output data of the detectors 20 is carried out in an evaluation device 18, preferably a computer, e.g. with the aid of the Fourier transformation, a blank characteristic, tomogram or a map of the mask blank 10 being created from the items of information generated. Such a tomogram may thereupon be used, in each step for producing the mask blank 10, as a reference for measurement data or blank alterations in the individual process steps.

If the mask blank 10 is fixed in a fixing device (not illustrated) with an adjustable clamping force, then a flexure of the mask blank 10 possibly brought about by the clamping may be identified and corrected if the evaluation device 18 is connected to the adjustable clamp or fixing device.

Figure 3:
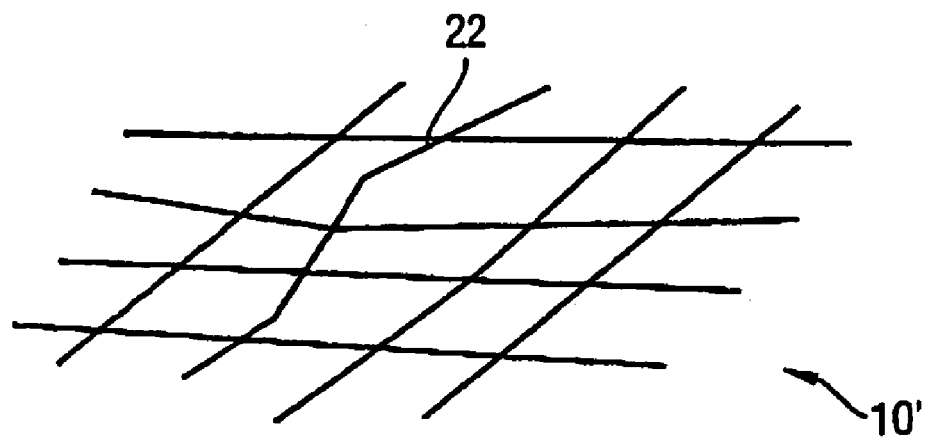
FIG. 3 shows a diagrammatic oblique view of a mask blank tomogram for elucidating the functioning of one embodiment of the present invention.

FIG. 3 illustrates a diagrammatic oblique view of a blank map 10', distortions, mechanical stresses in the mask blank 10 or flexures 22 of the mask blank 10 being illustrated by the flexed grid arrangement. In order to ensure a high quality standard of the mask blank 10, it is necessary to avoid distortions or flexures 22 of the mask blank 10, which can be identified in a blank map 10'.

Figure 4:
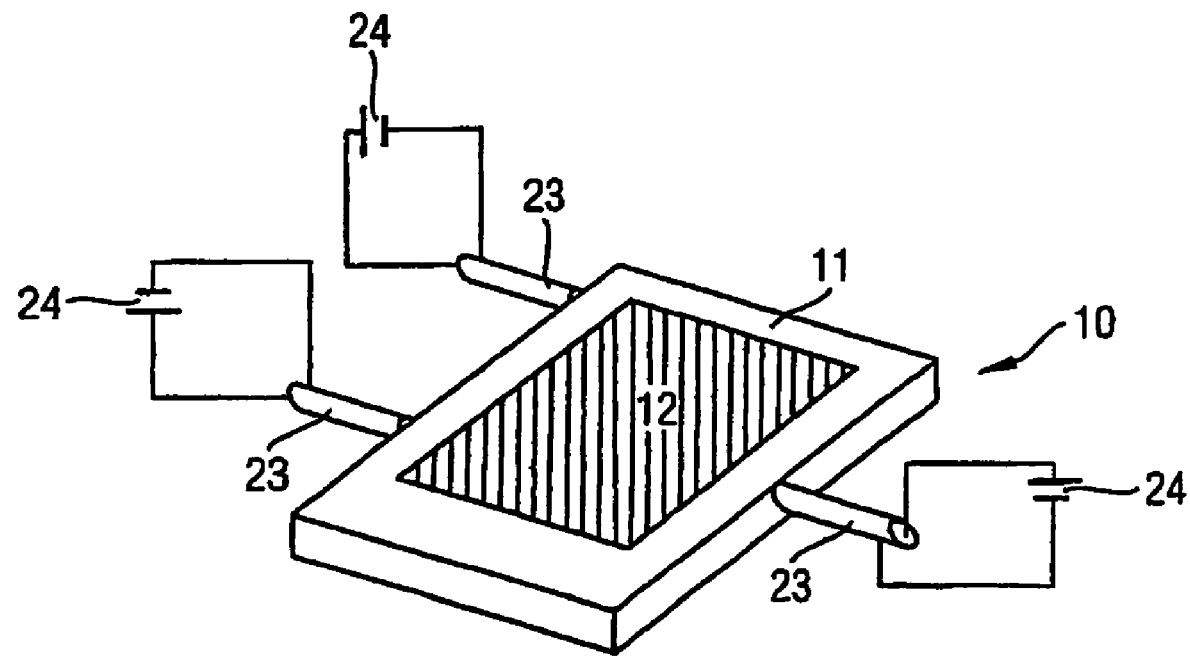
FIG. 4 shows a diagrammatic oblique view of a dynamic clamping device for a mask blank for elucidating a detail of one embodiment of the present invention.

FIG. 4 illustrates a detail, namely a fixing device 23 in the form of adjustable clamping elements, preferably piezoelements such as tube piezoelements, for example. The mask blank 10 is preferably fixed by means of three piezo devices 23, which can each be driven variably by means of a separate DC voltage 24. If an apparatus according to the invention, for example according to the embodiment as shown in FIG. 1 or 2, has localized a mechanical strain 22 of the mask blank 10 with the aid of a blank map 10' in accordance with FIG. 3, then the clamping elements 23, which can be driven independently of one another, can act on the mask blank 10 in such a way that the mechanical strain or flexure 22 is corrected or reduced. Application of a voltage 24 to the tube piezos used as clamping or fixing device 23 causes them to expand. A tube piezoelement has a tube structure in this case, the adjustable DC voltage 24 being connected to the outer wall, i.e. the tube exterior, by one pole and to the inner wall, i.e. the tube interior, by one pole. The regulation of the DC voltage 24 may be provided externally for example with the aid of a potentiometer (not illustrated). In this way, a variable clamping force and thus the mechanical stress in a mask blank 10 can be controlled actively and, consequently, detected flexures of the mask blank 10 can be reduced.

Although the present invention has been described above on the basis of preferred exemplary embodiments, it is not restricted thereto, but rather can be modified in diverse ways.

Thus, the illumination device is not restricted to laser-based devices, but rather may also be provided for example by an illumination device with long coherent wavetrains such as a mercury vapor lamp, for example. Furthermore, geometries other than rectangular arrangements and thus also geometries of the illumination device or of the detection device such as a circular configuration, for example, are also conceivable, in principle.

What is claimed is:

1. An apparatus for determining physical properties of a mask blank, comprising:
    an illumination device to radiate a predetermined light laterally into the mask blank;
    a detection device arranged diametrically opposite to the illumination device to detect the light which has been scattered and/or runs through the mask blank; and
    an evaluation device to determine physical properties of the mask blank from the light which has been scattered and/or has run through the mask blank and has been detected in the detection device, wherein
    the illumination device and the detection device are rotatable by at least 180 degrees in the plane of the mask blank around the mask blank situated in between.

2. The apparatus according to claim 1, wherein the illumination device has a laser device or laser diodes.

3. The apparatus according to claim 1, wherein the illumination device, the mask blank and the detection device are accommodated in a mask production tool.

4. The apparatus according to claim 1, wherein a data analysis of the light detected by the detection device on the basis of a Fourier transformation to create a characteristic of the mask blank is be provided in the evaluation device.

5. The apparatus according to claim 1, wherein the mask blank is fixed in a fixing device with an adjustable clamping force.

6. The apparatus according to claim 5, wherein the fixing device of the mask blank has at least three separately drivable clamping elements.

7. The apparatus according to claim 5, wherein the fixing of the mask blank in the fixing device is provided by piezoelements.

8. The apparatus according to claim 7, wherein the clamping force of the fixing device of the mask blank is adjustable depending on the evaluated predetermined properties of the mask blank.

9. A method for determining physical properties of a mask blank, comprising:
    radiating a predetermined light perpendicularly to a side wall of the mask blank and laterally into the mask blank by means of an illumination device;
    detecting the light, which has been scattered in the mask blank by means of a detection device arranged diametrically opposite to the illumination device;
    rotating the detection device and the illumination device around the mask blank by an angle of at least 180 degrees, the mask blank being in the same plane as the detection device and the illumination device;
    determining the properties of the mask blank from the detected scattered light in an evaluation device and
    storing the properties of the mask blank in a digital storage device.

10. The method according to claim 9, wherein a data analysis of data forwarded by the detection device based on a Fourier transformation to determine physical properties of the mask blank is executed in the evaluation device.

11. The method according to claim 9, wherein the determination of physical properties of the mask blank is effected in at least one machining and/or processing tool of the mask blank before the respective machining and/or processing of the mask blank.

12. The method according to claim 9, wherein properties of the mask blank, once they have been determined, are used as a reference for subsequent process and/or machining steps of the mask blank.

13. The method according to claim 9, wherein, utilizing the Kerr effect, light which runs through the mask blank in the detection device is detected.

14. The method according to claim 9, wherein scattering sources and/or flexures in the mask blank are calculated and localized in the evaluation device based on the received data of the detection device.

15. The method according to claim 14, wherein based on the data of a localized scattering source brought about by a mechanical flexure, an adjustable fixing device, which clamps the mask blank, is driven such that the flexure is reduced.

16. The method according to claim 15, wherein the adjustable fixing device has electrically drivable piezoelements for clamping the mask blank, by which mechanical stresses and/or flexures in the mask blank are corrected.

17. A method for determining physical properties of a mask blank, comprising:
    radiating a predetermined light perpendicularly to a side wall of the mask blank and laterally into the mask blank by an illumination device;
    detecting the light, which has been scattered in the mask blank by a detection device arranged diametrically opposite to the illumination device;
    rotating the detection device and the illumination device around the mask blank by an angle of at least 180 degrees, the mask blank being in the same plane as the detection device and the illumination device; and
    determining the properties of the mask blank from the detected scattered light in an evaluation device,
    wherein scattering sources and/or flexures in the mask blank are calculated and localized in the evaluation device based on the received data of the detection device, and
    wherein based on the data of a localized scattering source brought about by a mechanical flexure, an adjustable fixing device, which clamps the mask blank, is driven such that the flexure is reduced.

18. The method according to claim 17, wherein the adjustable fixing device has electrically drivable piezoelements for clamping the mask blank, by which mechanical stresses and/or flexures in the mask blank are corrected.

* * * * *